United States Patent
De Assis Angeloni et al.

(10) Patent No.: US 12,100,508 B2
(45) Date of Patent: Sep. 24, 2024

(54) METHOD FOR PREDICTING MAXIMAL OXYGEN UPTAKE IN WEARABLE DEVICES

(71) Applicant: SAMSUNG ELETRÔNICA DA AMAZÔNIA LTDA., São Paulo (BR)

(72) Inventors: Marcus De Assis Angeloni, Campinas—São Paulo (BR); Antonio Joia Neto, Campinas—São Paulo (BR); Ciro Cavani, Campinas—São Paulo (BR); Dong Hyun Lee, Seoul (KR); In Taek Oh, Seongnam-si (KR)

(73) Assignee: SAMSUNG ELETRÔNICA DA AMAZÔNIA LTDA., Campinas (BR)

( * ) Notice: Subject to any disclaimer, the term of this patent is extended or adjusted under 35 U.S.C. 154(b) by 869 days.

(21) Appl. No.: 17/197,555

(22) Filed: Mar. 10, 2021

(65) Prior Publication Data
US 2022/0199244 A1 Jun. 23, 2022

(30) Foreign Application Priority Data

Dec. 23, 2020 (BR) ...................... 10 2020 026639 0

(51) Int. Cl.
| | |
|---|---|
| *G06F 1/16* | (2006.01) |
| *G06N 3/08* | (2023.01) |
| *G06N 5/02* | (2023.01) |
| *G16H 10/60* | (2018.01) |
| *G16H 40/63* | (2018.01) |

(52) U.S. Cl.
CPC ............ *G16H 40/63* (2018.01); *G06F 1/163* (2013.01); *G06N 3/08* (2013.01); *G06N 5/02* (2013.01); *G16H 10/60* (2018.01); *A63B 2230/06* (2013.01)

(58) Field of Classification Search
CPC ................. G06F 1/163; G06F 2200/16; G06F 2212/1044; G06F 2212/1056; G06N 3/08; G06N 5/02; G06N 20/20
See application file for complete search history.

(56) References Cited

U.S. PATENT DOCUMENTS 9,517,028 B1 12/2016 Saalasti et al.
2011/0040193 A1 2/2011 Seppanen et al.
(Continued)

OTHER PUBLICATIONS

Mehmet Fatih Akay, et al., "Artificial neural network-based model for predicting VO₂max from a submaximal exercise test", Expert Systems with Applications, 2011, 4 pages.
(Continued)

*Primary Examiner* — Paul B Prebilic

(57) ABSTRACT

A method for predicting maximal oxygen uptake (VO$_2$Max) in wearable devices with memory restriction using an ensemble of machine learning algorithms is described. The method is related to the fields of well-being, healthcare and artificial intelligence, and includes a technique that predicts maximal oxygen uptake (VO$_2$Max) in running sessions at different paces using wearable devices with memory restriction. The proposed method requires less than 5 KB of memory to run on a wearable device. Specifically, based on user's profile data (age, gender, height and weight), a set of heart rate (HR) and speed readings of a running session, the method is able to estimate VO$_2$Max.

10 Claims, 5 Drawing Sheets

(56) References Cited

U.S. PATENT DOCUMENTS

| | | | |
|---|---|---|---|
| 2015/0088006 A1* | 3/2015 | Rapoport | A61B 5/1112 600/484 |
| 2016/0206248 A1* | 7/2016 | Sartor | A61B 5/681 |
| 2019/0009134 A1* | 1/2019 | Battaglini | A61B 5/024 |
| 2022/0199244 A1* | 6/2022 | De Assis Angeloni | G16H 50/30 |
| 2023/0191195 A1* | 6/2023 | De Oliveira Rosa Prates | G16H 40/67 702/19 |

OTHER PUBLICATIONS

Pat R. Vehrs, et al., "Submaximal Treadmill Exercise Test to Predict $VO_2$max in Fit Adults", Measurement in Physical Education and Exercise Science, https://doi.org/10.1080/10913670701294047, 2007, 13 pages.

* cited by examiner

METHOD FOR PREDICTING MAXIMAL OXYGEN UPTAKE IN WEARABLE DEVICES

CROSS-REFERENCE TO RELATED APPLICATION(S)

This application is based on and claims priority under 35 U.S.C. § 119 to Brazilian Patent Application No. 10 2020 026639 0, filed on Dec. 23, 2020, in the Brazilian Intellectual Property Office, the disclosure of which is incorporated by reference herein in its entirety.

TECHNICAL FIELD

The present invention relates to a healthcare technology with application for estimating the cardiorespiratory fitness of users using wearable devices. More specifically, a method for predicting maximal oxygen uptake (VO$_2$Max) in wearable devices with memory restriction using an ensemble of machine learning algorithms is described.

BACKGROUND

Wearable devices are the mainstream technology to help people improve their health and well-being by measuring and analyzing their biological signals captured using non-invasive sensors (for example, accelerometers and light pulses). VO$_2$Max is a necessary component to provide a complete healthcare package on wearable devices.

Different activities have different oxygen consumption and increasing the intensity of an activity results in more oxygen being taken. In this sense, VO$_2$Max is related to the VO$_2$ reached when oxygen consumption remains in a stable state, despite an increase in effort load.

For running activity, there are two relevant entries for determining workload intensity: speed and heart rate. Increasing the speed also increases the heart rate, as a body response to a particular stimulus. Depending on the individual's physical condition, both entries have different behaviors in time and variation. For example, individuals with better physical fitness will have higher speeds for longer and heart rate with less variation. In addition to these, other important entries are gender, age, weight and height.

Time series of speed and heart rate with information about the user compose a high dimension space where the most reliable regions to estimate the correct VO$_2$Max must be found.

The main challenge in this technology is to be equally efficient with different types of people (for example, different genders, age groups and body masses). Therefore, the appropriate choice of algorithms is the way to improve this technology in order to cover a more heterogeneous population.

As maximal oxygen uptake has become an important reference standard for cardiorespiratory fitness, researchers have been developing and registering studies of maximal protocols in order to improve the prediction of VO$_2$Max value. These types of protocols, in general, directly measure gas exchange rates during an individual's breathing using reference equipment and high-intensity workloads, which is an expensive and physically exhausting exam for participants.

The complexity of direct measurements, as well as the excessive physical demands made on subjects, led to the development of several indirect methods of estimating VO$_2$Max based on submaximal protocols.

Consequently, many studies have emerged with a focus on VO$_2$Max prediction from submaximal exercise protocols, which differ considerably according to the proposed exercise and stimulus. Some works use different submaximal protocols such as exercise bike, aerobic dance, futsal, treadmill, among others.

The use of different submaximal protocols can result in different values of VO$_2$Max, since each exercise requires a different amount of muscle mass activation. In addition, some other initiatives attempt to estimate VO$_2$Max using protocols that do not involve exercise. However, the present invention focuses on estimating VO$_2$Max based on a running or walking exercise that can be done on a treadmill or in an outdoor environment.

US patent document 20110040193 entitled "Fitness Test", published on Feb. 17, 2011, by FIRSTBEAT TECHNOLOGIES OY, describes a method having a pre-processing step to find "reliability segments", excluding low reliability and then combining multiple segments to perform a weighted estimation of VO$_2$Max from heart rate data. However, the method presented by this application uses a simpler pre-processing step based on signal variance and requires little memory to calculate the most reliable data. The other big difference is that the method of the present invention uses a machine learning ensemble to estimate VO$_2$Max, based on pattern detection to improve overall performance in different demographics. The present invention combines a simpler pre-processing step and a more powerful estimator, while being more applicable to the devices with memory restriction.

Patent document U.S. Pat. No. 9,517,028, published on Dec. 13, 2016, by FIRSTBEAT TECHNOLOGIES OY, describes a method for calculating the Anaerobic Threshold (AnT) from the heart rate signal. The main similarity with the present invention concerns the selection of heart rate segments with "higher probability factors" and then computing the AnT of those segments. AnT has similar principles with VO$_2$Max and is an average for assessing exercise intensity.

The main difference with the proposed method lies in the selection of points. U.S. Pat. No. 9,571,028 uses maximum probabilities with instantaneous variability as an output depending on the exercise, but the present invention uses minimal variance, having as output a fixed point during a certain period of days.

The article "Submaximal Treadmill Exercise Test to Predict VO2Max in Fit Adults", published in December 2007 by P. Vehrs, J. George, G. Fellingham and S. Plowman & K. Dustman-Allen, describes a collection of data sets and a method to estimate VO2Max using linear regression. In the present application, a similar procedure was used to collect a data set and where there was a good fit. One of the models used in our machine learning set has characteristics similar to those used in the publication, but it is suitable for the data set of this application. The main differences of the present order for publication are: the combination of other machine learning models, a pre-processing to extract good data and an output processing to combine predictions of the same patient in multiple exercises over time.

The article "Artificial neural network-based model for predicting VO2Max", published in March 2011, by M. Akay, E. Zayid, E. Akturk & J. George, proposes a model based on artificial neural network to predict VO$_2$Max from a submaximal treadmill exercise test. Although the present application also uses artificial neural networks, a combination of two neural networks is used herein, different inputs and criteria for obtaining temporal information, and a different architecture in terms of the number of neurons and the activation function.

Gold standard methods to accurately estimate maximum oxygen uptake ($VO_2Max$) require expensive equipment, exhaustive exercise protocols and medical supervision. In this sense, we propose a method based on machine learning that estimates $VO_2Max$ from physical exercises at the user's own pace, using wearable devices or other devices with memory restrictions, requiring less than 5 KB of memory to run.

Maximum oxygen uptake is the maximum rate at which oxygen can be consumed by an individual. This rate is strongly related to the aerobic metabolism capacity of the human body, indicating the maximum capacity to synthesize energy in the presence of oxygen. $VO_2Max$ is achieved by intense exercises, so that any additional work after reaching it can only be done without the use of oxygen, that is, by anaerobic breathing.

$VO_2Max$ is a common fitness index for athletes. The higher its value, the more conditioned the athlete is. On the other hand, a low $VO_2Max$ value is associated with an increased risk of cardiovascular disease.

Gold standard methods for measuring $VO_2Max$ use complex cardiorespiratory devices to acquire gas exchange data. These involve measures of oxygen absorption in breathing ($VO_2$), expenditure of carbon dioxide ($VCO_2$) and pulmonary ventilation during an increased physical workload to the maximum in a progressive exercise stimulus. To accurately measure the $VO_2Max$ value, the individual must meet some physical criteria when performing the maximum protocol. These criteria are:

- minimum exercise duration;
- reaching the maximum heart rate (with a tolerance of about 10 beats per minute);
- reaching the Borg scale for muscle or breathing effort above 8 (scale from 1 to 10);
- $VO_2$ readings indicating the presence of a plateau;
- ratio between the $CO_2$ output volume and the $O_2$ input volume (respiratory exchange ratio) greater than 1.1.

However, this method of measuring $VO_2Max$ is expensive and requires too much physical effort, since the equipment to measure gas exchange is very expensive and the exercise protocol necessary to reach $VO_2Max$ requires a level of much more effort than a traditional exercise.

To get around this problem, a method is proposed to obtain a reasonably accurate prediction of $VO_2Max$ using cheaper wearable devices while the individual does an exercise protocol with less physical effort.

SUMMARY

The present invention is related to the fields of well-being, healthcare and artificial intelligence. It includes a technique that predicts maximum oxygen uptake ($VO_2Max$) in running sessions at different paces using wearable devices with memory restriction. The proposed method requires less than 5 KB of memory to run on a wearable device.

Specifically, based on the user's profile data (age, gender, height and weight), a set of heart rate readings (Heart Rate, HR) and the speed of a running session, the proposed method is capable to estimate $VO_2Max$.

In addition, the method performs lightweight filtering of heart rate and speed signals using variance to select the most reliable data and a combination of lightweight machine learning approaches, for example, linear regression and artificial multilayer Perceptron neural networks for detect patterns from these data and predict $VO_2Max$.

It is worth noting that several forecasts are combined over time, thus obtaining a more reliable $VO_2Max$ prediction as more points and regions are considered.

The machine learning models were trained using a proprietary data set that allowed the understanding of the correlations between the $VO_2$ information collected by professional equipment and information from wearable sensors.

In addition, this invention uses a machine learning ensemble to estimate $VO_2Max$, depending on pattern detection to improve overall performance in different demographics.

The method can obtain a reasonably accurate prediction of $VO_2Max$ using only data and sensors available on most smartwatches, such as profile data, heart rate (HR) based on photoplethysmography (PPG) sensor and computed speed using accelerometer sensors or libraries of the Global Positioning System (GPS). Another advantage is that the method does not require the maximum effort of a subject, allowing the user to run at the location of their choice and at the pace at which they are used to train. In addition, the method uses a combination of low memory features with lightweight machine learning approaches to make predictions, which require less than 5 KB of memory and are deployable on memory-constrained devices or even microcontrollers.

BRIEF DESCRIPTION OF THE DRAWINGS

The objectives and advantages of the present invention will be made clearer through the following detailed description of the example and non-limiting drawings presented at the end of this document.

DETAILED DESCRIPTION

Figure 1:
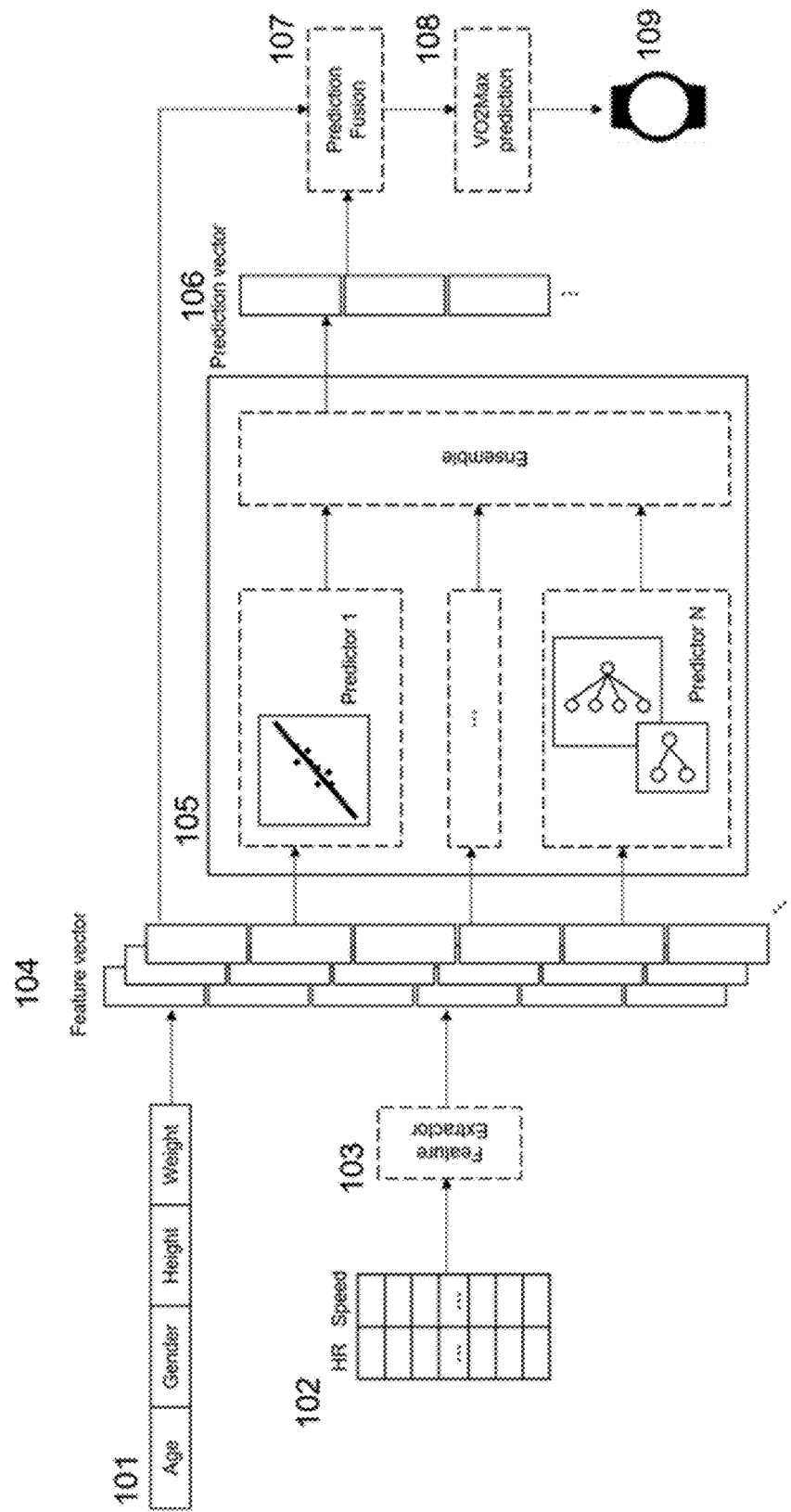
FIG. 1 presents the flow chart for estimating $VO_2Max$, in which the inputs of the machine learning approaches and the steps to display the prediction result are presented.

In FIG. 1, an overview of the operation of the method of the present invention is presented. First, user profile information 101 is provided, including age, gender, height and weight. Second, two temporal inputs are captured, composed of heart rate and speed readings 102, then split into n-second time windows without overlap, which are processed by a feature extractor module 103. The feature extractor module includes finding points in the time series where heart rate and speed are more correlated with $VO_2Max$.

To find these points of greatest correlation, regions are selected where the heart rate signal and speed have remained more stable.

In this sense, the signal stability is calculated using a threshold in the standard deviation of M minutes of the signal sampled at 1 Hz. As long as the standard deviation of the signal is less than the threshold, this region is classified as stable.

For each stable region, the point with the lowest standard deviation is selected, and the window containing it is used to calculate the average heart rate and speed as features. Finally, the profile data are concatenated to these averages as feature vectors 104.

These feature vectors are used as input to an ensemble of machine learning models 105, such as linear regression and artificial multilayer Perceptron neural networks (MLP). While the user is running, each predicted value in the ensemble is added to a prediction vector 106.

Based on some rules, such as minimum time to show $VO_2Max$ to the user, a prediction fusion module 107 uses a weighted sum in the prediction vector and provides a new $VO_2Max$ 108 prediction to be shown on the user's wearable device 109.

With information about $VO_2Max$ on the wearable device, the user can monitor their fitness status, improvements, and possible adaptations in their training.

Figure 2:
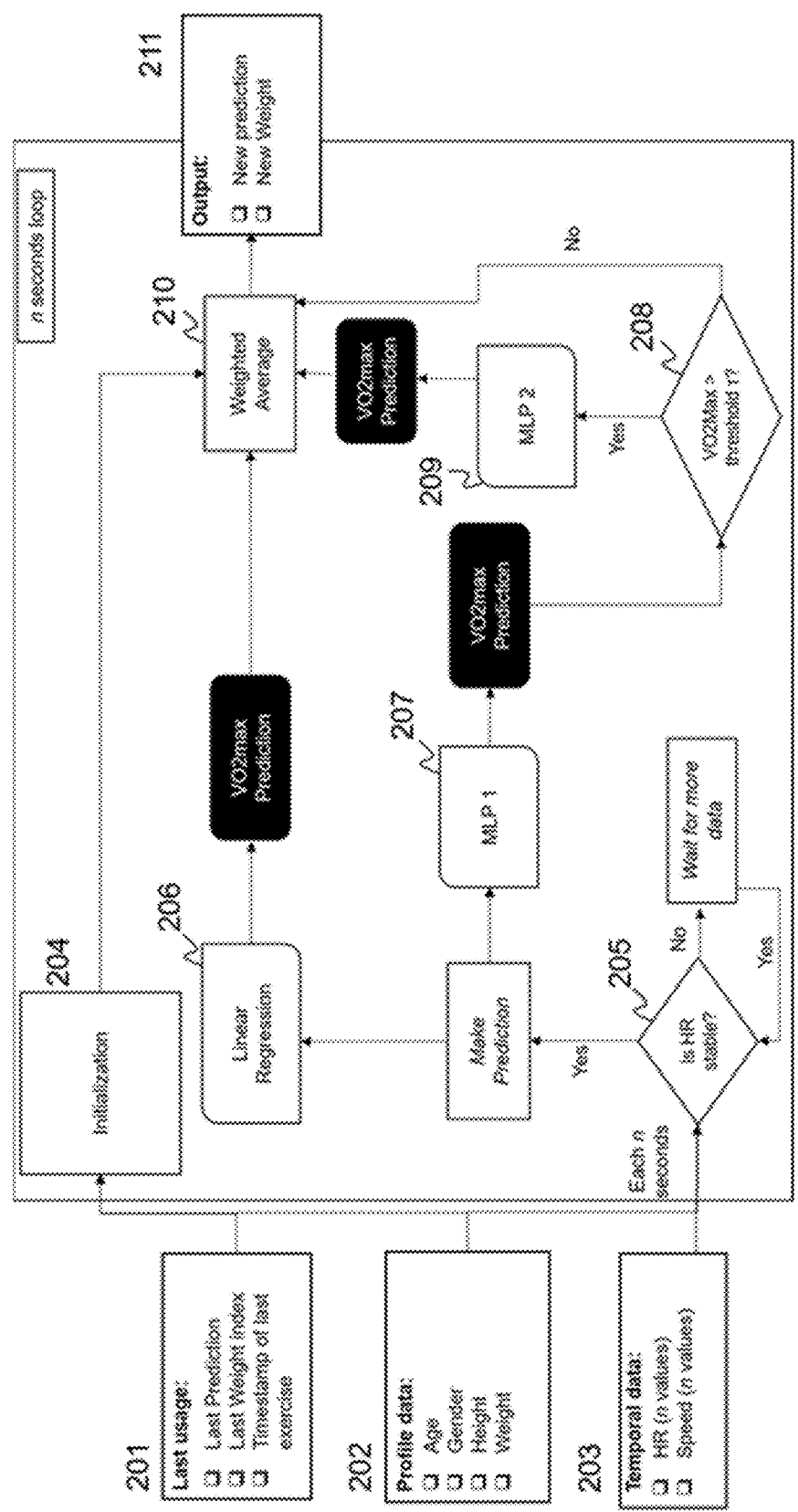
FIG. 2 illustrates a flow chart in more detail about the functioning of the proposed approach.

In FIG. 2, the operation of the proposed method is illustrated in more detail. The last prediction shown to the user 201, when available, is given to the initialization method 204. Its value, as well as the adopted coefficient and the timestamp of when the last exercise was performed, are used in the fusion module 107, represented by the weighted average module 210. User profile data 202, composed of age, gender, height, and weight, is required at initialization 204, where preliminary calculations are performed, such as initializing inputs for the multilayer Perceptron artificial neural network (MLP) (207, 209), and the computation of bias for the linear regressor (206).

In addition, profile data (for example, age, gender, height, and weight) is constant in the data batch that is used as exercise information. However, as the sensor data varies throughout the exercise, the temporal data (203), such as heart rate (HR) and speed, are sampled at 1 Hz and split into n-second windows.

Moreover, some restrictions are set to check the minimum and maximum values expected for heart rate and speed in a running session, thus avoiding incorrect calculations due to a sensor reading error. Furthermore, verification 205 is performed, as the values are subject to noise in the warm-up and recovery stages of the exercise, causing a variation in these values that may not correspond to the user's general physical state.

Even if the heart rate is not stable, the method waits for the time data from the next n-second window.

When a stable interval is found, its most stable point is estimated and when reaching the end of this interval, a signal to make the prediction is defined and then a set of predictors are executed, as for example (but not limited to them) linear regression 206 and the first MLP.

In order to reduce memory consumption and calculate the mean and standard deviation of the time series, instead of storing M minutes of the sampled signal at 1 Hz, only the sum of the signal and the sum of the squared signal are used.

For example, considering that each window of temporal data has N seconds, the moving average $\bar{x}_{A \rightarrow A+M}$, that is the average of the temporal signal with a sliding window of M seconds with a stride of N seconds starting at the second A, can be calculated using the following equation:

$$\bar{x}_{A \rightarrow A+M} = \bar{x}_{A \rightarrow A+N-1} + \bar{x}_{A+N \rightarrow A+2N-1} + x_{A+2N \rightarrow A+3N-1} + \ldots + \bar{x}_{A+M-N+1 \rightarrow A+M}$$

where the mean of the time series $\bar{x}_{X \rightarrow Y}$ from point X to point Y is defined as:

$$\bar{x}_{X \rightarrow Y} = \frac{1}{Y - X + 1} \sum_{i=X}^{Y} x_i$$

Using this representation, the moving average is calculated storing M/N variables.

To calculate the standard deviation, the following equation is expanded:

$$STD(\bar{x}) = \left(\frac{1}{M}\sum_{i=1}^{M}(x_1 - \bar{x})^2\right)^{\frac{1}{2}} = \left(\frac{1}{M}\left(\sum_{i=1}^{M}x_i^2 - 2\bar{x}\sum_{i=1}^{M}x_i + M\bar{x}^2\right)\right)^{\frac{1}{2}}$$
$$= \left(\frac{1}{M}\overline{x^2} - \bar{x}^2\right)^{\frac{1}{2}}$$

Next, to calculate the standard deviation of the temporal signal with a sliding window of M seconds with a step of N seconds starting at the second A, the following equation is used:

$$STD(x_{A \rightarrow A+M}) = \left(\frac{1}{M}\overline{x^2}_{A \rightarrow A+M} - \bar{x}^2_{A \rightarrow A+M}\right)^{\frac{1}{2}}$$

wherein $$\overline{x^2}_{A \rightarrow A+M} = \overline{x^2}_{A \rightarrow A+N-1} + \overline{x^2}_{A+N \rightarrow A+2N-1} + x2_{A+2N \rightarrow A+3N-1} + \ldots + \overline{x^2}_{A+M-N+1 \rightarrow A+M}$$

and the mean of the square time series from point X to point Y is defined as $\overline{x^2}_{X \rightarrow Y}$ $$\overline{x^2}_{X \rightarrow Y} = \frac{1}{Y - X + 1} \sum_{i=X}^{Y} x_i^2$$

Using this representation, it is possible to calculate the moving standard deviation just by storing 2*M/N variables, where M/N came from $\overline{x^2}_{A > A+M}$ and M/N from $\bar{x}_{A \rightarrow A+M}$.

Linear regression (206) is proposed based on a feature engineering process to select the inputs considering the tradeoff between performance and memory constraints, and a cross-validation approach to define the coefficient for each input.

Among the evaluated inputs, the extended features and some combinations of them, the following six inputs are used for the linear regression: heart rate, speed, age, gender, weight and the ratio between HR and speed (HR/S). The relationship between HR and speed allows us to contemplate the relationship between stimulus (speed) and response (HR) at different times of the exercise, which together with the filtering of the stabilization method brings more confidence and robustness in the prediction.

After selecting the inputs for linear regression, a linear least squares model is trained. The training set is divided into a new training and validation subset, and a linear model with coefficients for each input is assembled in order to minimize the residual sum of squares between the $VO_2Max$ ground truth of the validation set, and the values predicted by the linear approximation. The best approximation was found using a regressor that used a subset of selected entries (age, gender, speed, weight and heart rate), and retraining the data set according to the new entries (for example, heart rate/speed). Thus, the prediction of linear regression in the present invention is obtained by the following equation:

$$VO2Max = n_0 + (n_1 * G) + (n_2 * S) - (n_3 * W) - (n_4 * HR) - (n_s * A) + (n_6 * HR/S)$$

where $VO_2Max$ is in ml/min/Kg, G refers to gender (0=female and 1=male), S refers to speed in Km/h, W refers to weight in Kg, HR refers to the heart rate in beats per minute, A refers to age in years, and $n_0$ to $n_6$ refer to constant values used for the adjustment (coefficients of linear regression).

The multilayer Perceptron neural network (MLP) 207 works as a non-linear regression model and improves the results since the relationship between $VO_2Max$ and the input features are not linear. Due to memory restrictions, the number of hidden layers and neurons to be used is very limited, consequently reducing the MLP's ability to approximate more complex functions.

To deal with this limitation, a simple hierarchical approach of neural networks is used, combining two MLPs, in which each MLP has a hidden layer.

Each MLP has been trained in a specific set of participants with different $VO_2Max$ ranges, to simplify the mapping function that the MLP needs to approximate, while helping to avoid overfitting.

Thus, a strategy for making a prediction is defined with a first MLP and based on a verification of the predicted value against a predefined threshold T (208). Therefore, a new prediction with a second MLP (209) is made to refine the estimate only when necessary. Inputs for both MLP are age, gender, height, weight, HR and speed.

Due to an intrinsic behavior of the human cardiovascular system, depending on environmental and psychological conditions, changes can be registered in the readings of the sensors of the wearable devices causing changes in the heart rate levels even at a constant speed. This can become a problem, since the HR response to speed can be influenced by external factors in some situations in the data set collected for the present invention, and considering that only one submaximal test data was captured for each individual, which can lead to an outlier data.

To deal with this problem, thousands of models are trained by removing a random percentage of subjects from the training set at each attempt and trying to choose the model that best fits the validation set.

The first MLP of the final architecture, used as an example in the present invention, includes a hidden layer with two neurons that has been trained with subjects that have $VO_2Max$ less than τ+tolerance. If the $VO_2Max$ prediction of the first MLP is greater than τ, the prediction is given by a second MLP containing a hidden layer with four neurons and trained with participants who have $VO_2Max$ greater than τ−tolerance.

The solution proposed in the innovation allows forecasts with other machine learning models, but due to memory restrictions, only the combination using linear regression and MLP is presented.

With the predictions of each machine learning model and the prediction of previous exercises (when available), a weighted average of 210 is performed to fuse the predictions.

First, the prediction of linear regression and MLP are combined for each stable region of n-seconds, where the average of their predictions is made as follows:

$$VO_2Max'_\tau = \frac{(VO_2Max_{LR} + VO_2Max_{MLP})}{2}$$

where $VO_2Max_\tau'$ is the fused prediction for the T window, $VO_2Max_{LR}$ is the prediction of linear regression and $VO_2Max_{MLP}$ is the prediction of MLP.

After that, a $weight_\tau$ related to the confidence of this region is reached based on the percentage of theoretical maximum heart rate (pHR) as follows:

$$pHR = \frac{\overline{HR}}{211 - 0.64 * Age}$$

where $\overline{HR}$ is the average of heart rate readings in a n-second window and the denominator is an estimation of the maximum heart rate according to age.

The use of a base parameter to assign weights to each prediction is based on a correlation analysis of some features in relation to the algorithm error; higher values of pHR had a correlation with a smaller error.

In a preferred embodiment of the present application, the value attributed to weight, is shown in Table 1 according to pHR:

| % of Maximum Heart Rate (pHR) | Weight |
|---|---|
| pHR > 90% | 16 |
| 80% < pHR ≤ 90% | 8 |
| 70% < pHR ≤ 80% | 4 |
| pHR ≤ 70% | 3 |

Finally, a weighted sum $VO_2Max_\tau'$ is made with previous $VO_2Max$ forecasts. The last prediction shown to the user (201), when available, has its weight reduced according to the time that the person is not exercising. This reduction factor is linear according to the number of days since the last prediction was recorded. After 30 days without exercising, the value drops to zero. With each new running session, the sum of the weights is readjusted with time decay as follows:

$$weight_{\tau-1} = \max\left(0, weight'_{\tau-1} * \left[1 - \frac{\text{days since the last prediction}}{30}\right]\right)$$

Thus, the weighted sum to obtain $VO_2Max$ output per time (211) is:

$$VO_2Max_\tau = \frac{weight_\tau * VO_2Max'_\tau + weight_{\tau-1} * VO_2Max_{\tau-1}}{(weight_\tau + weight_{\tau-1})}$$

where $weight_\tau$ is the computed weight for the current stable region, $weight_{\tau-1}'$ is the accumulated weight up to the previous stable region, $VO_2Max_\tau'$ is the current prediction, and $VO_2Max_{\tau-1}$ is the last computed prediction.

It is important to mention that for the next stable region, $VO_2Max_\tau$ will become $VO_2Max_{\tau-1}$. The new value of $weight_\tau'$ will be the sum of $weight_{\tau-1}'$ and $weight_\tau$. In order to prevent the weight value from increasing too much so that new forecasts no longer have effect, the minimum between the sum of all weights and MaxWeight is applied. The equation for updating $weight_\tau'$ becomes the following:

$$weight_{\tau-1}' = \min(weight'_{\tau-1} + weight_\tau, MaxWeight)$$

where $weight_{\tau-1}'$ is the accumulated weight until the previous stable region and $weight_\tau$ is the weight adopted for the last $VO_2Max$ computation.

Figure 3:
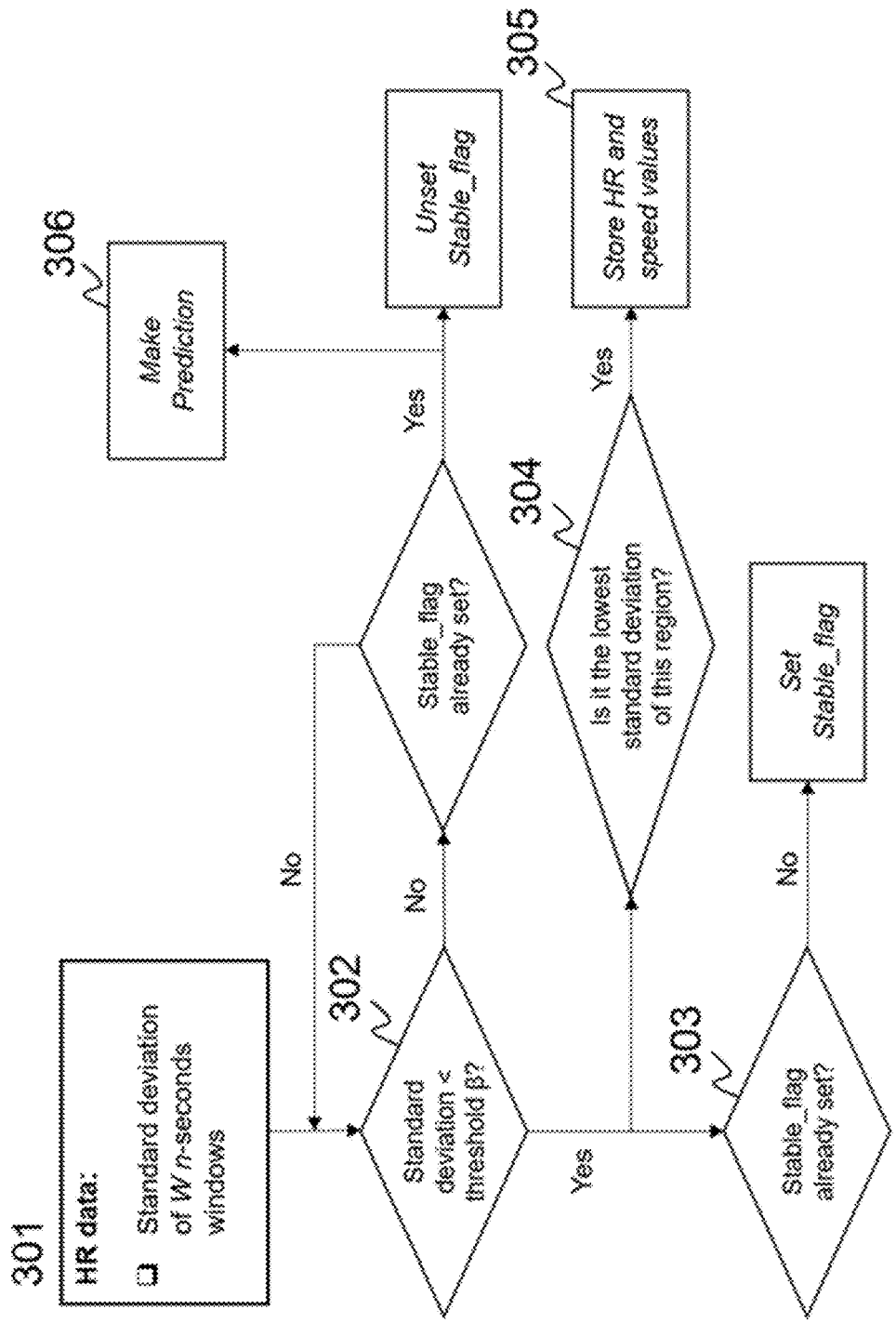
FIG. 3 shows how the stable features check works.

FIG. 3 provides additional details on checking stable values. A flag is used to indicate when a stable region starts and ends and then stores the average HR and speed values with the lowest standard deviation for this region.

Stable regions are regions where the HR does not vary much for a predefined time, composed of a set of W n-second windows. Thus, the input for the checking is the HR data (301) with the standard deviation between the last W time windows.

First, the standard deviation is compared with a predefined threshold β (302). If the standard deviation is less than β, the flag is defined as stable if it has not yet been defined (303), and it is verified if this is the smallest standard deviation for this region (304).

If it is the smallest standard deviation, the current values of HR and speed (305) to be used in the next prediction (306) are stored. On the other hand, if the standard deviation is greater than R (302), the status of the stable flag is checked and, if it is not set, the next HR data is awaited. If the stable variable is enabled, prediction (306) is made and the flag is redefined, indicating the end of the current stable region.

In summary, since the HR standard deviation is below the R threshold, a stable region is started. The end of this stable region occurs when the standard deviation of HR becomes greater than the threshold. Within the stable region, the method stores the HR and the speed of the instant that have the smallest standard deviation, which will be used to make the prediction. The prediction is made when the stable region ends. Therefore, the method provides the same number of predictions as the number of stable regions. The main benefit of the stability algorithm to extract features is to maintain a good quality of prediction by using fewer cycles (instead of running all the time), resulting in less energy consumption.

Figure 4:
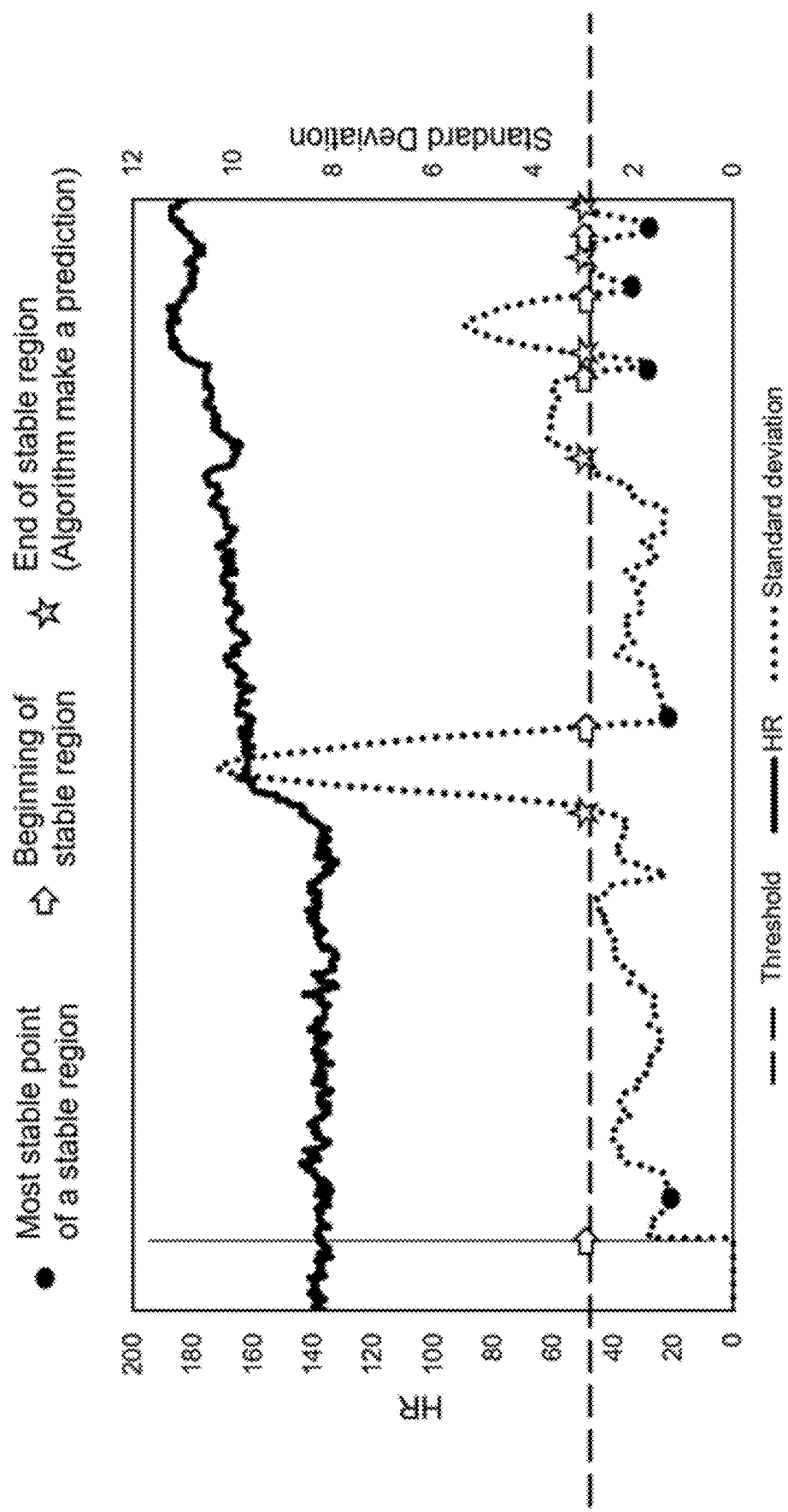
FIG. 4 shows an example of checking stable values.

In FIG. 4, an example graph can be seen containing five stable regions during an exercise, highlighting the beginning and end of each region, as well as the most stable point.

Additionally, since $VO_2Max$ is a parameter that has a low variance in a short time, if the algorithm calculates forecasts that vary widely, the confidence of the result will decrease. This undesirable behavior can occur not because of an algorithm error, but due to an intrinsic behavior of the heart that, for different environmental conditions (for example, temperature, weather, stress, running downhill) may show fluctuations in the readings (with the sensors available), and thus can change the value at which the heart rate will stabilize at a constant speed.

In this sense, the algorithm needs some time to obtain a statistically accurate and stable result when in an uncontrolled environment, and that means when the user runs the first few times, the method can compute predictions that vary widely.

To solve this variation problem, a method is proposed that presents to the user a smoother function of the predicted value.

Figure 5:
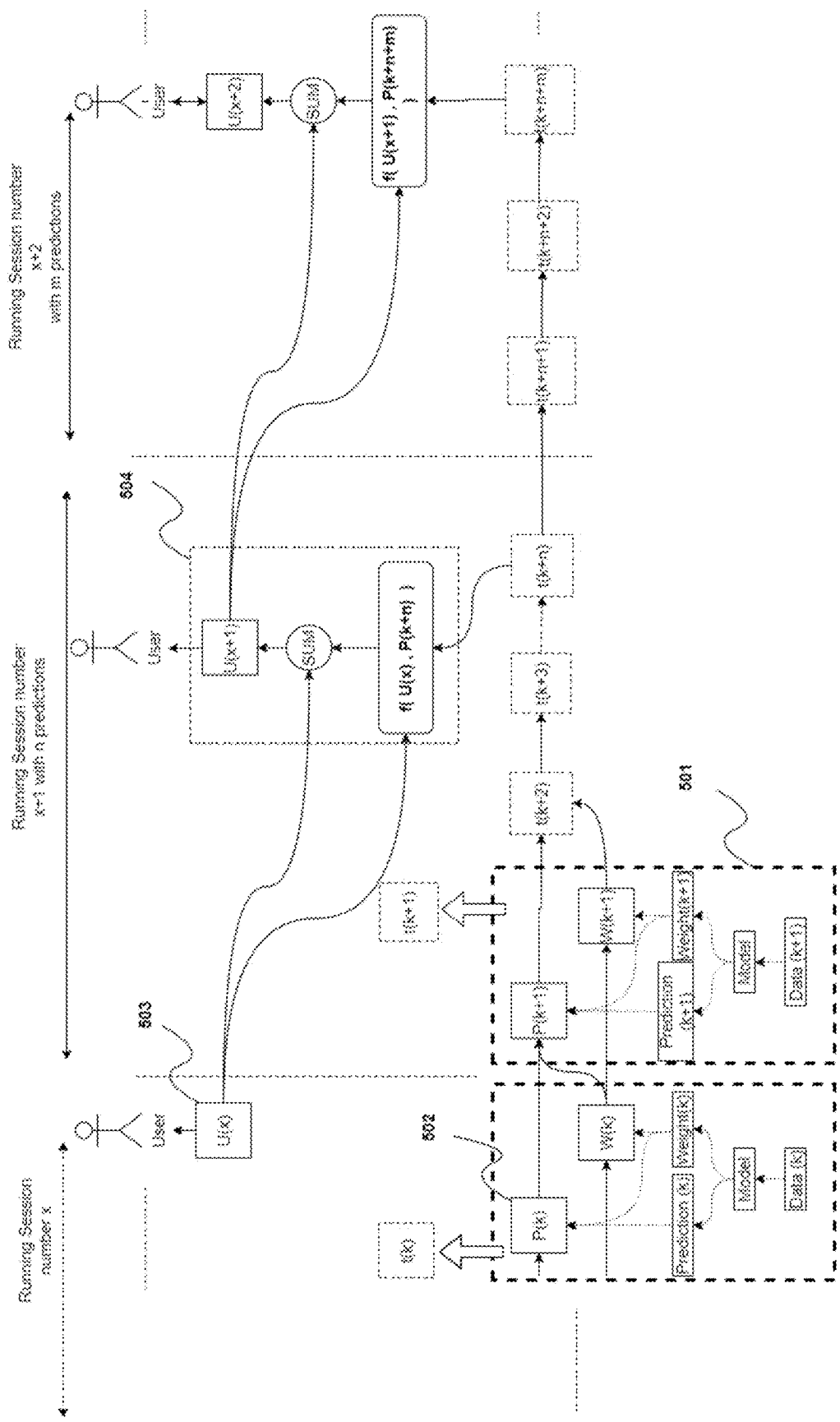
FIG. 5 presents details of the display of the results of the algorithm to the user.

Consider that the steps shown in FIG. 2 are contained in the block (501) represented in FIG. 5. For each new stable region 'k', there is an associated prediction P (k) (502), and for each session running 'x', there is an associated value presented to user U(x) (503). To define how the value presented to the user is updated, the 'x+1' running session has 'n' stable regions. Thus, to improve the user experience, the value being displayed to user U(x+1) (504) is updated according to the last user value U(x) (503) and the last prediction of the algorithm P(k+n) (501):

$$dU = f(U(x), P(k+n))$$

$$U(x+1) = dU + U(x)$$

where f function is defined as a function which follows the relation:

$$|f(U(x), P(k+n))| \leq |P(k+n) - U(x)|; \text{ and}$$

$$\frac{P(k+n) - U(x)}{|P(k+n) - U(x)|} = \frac{f(U(x), P(k+n))}{|f(U(x), P(k+n))|}$$

A simple example of f can be:

$$f(U(x), P(k+n)) = \frac{P(k+n) - U(x)}{2}$$

Thus, it becomes possible to control the maximum variance between consecutive $VO_2Max$ predictions shown to the user.

Additionally, the present invention includes at least one example of the numerous possibilities for combining machine learning techniques that can be implemented as an artificial intelligence (AI) module. A function associated with AI can be performed through non-volatile memory, volatile memory and the processor.

The present invention can include a processor or a plurality of processors. In this sense, one or a plurality of processors can be a general-purpose processor, such as a central processing unit (CPU), an application processor (AP), a graphics-only processing unit, such as a graphics processing unit (GPU), a visual processing unit (VPU) and/or a dedicated AI processor, such as a neural processing unit (NPU).

In addition, processors control the processing of input data according to a predefined operating rule or by an artificial intelligence (AI) model stored in non-volatile and/or volatile memory. The predefined operating rule or artificial intelligence model is provided through training or learning.

In this case, being provided through learning means that, when applying a learning algorithm to a plurality of learning data, a predefined operating rule or AI model of a desired feature is performed. Learning can be performed on a device on which artificial intelligence is performed and/or can be implemented through a separate server/system.

The AI model can include a plurality of layers of neural network, in which each layer has a plurality of weight values and performs a layer operation by means of calculations of a previous layer and an operation using a plurality of weights. Examples of neural networks include, but are not limited to, convolutional neural network (CNN), deep neural network (DNN), recurrent neural network (RNN), restricted Boltzmann machine (RBM), deep belief network (DBN), neural network bidirectional deep recurrent (BRDNN), generative adversarial networks (GAN) and deep Q networks.

The learning algorithm is a technique for training a predetermined target device (for example, a robot) using a plurality of learning data to cause, allow or control the target device to make a determination or prediction. Examples of learning algorithms include, but are not limited to, supervised learning, unsupervised learning, semi-supervised learning or reinforcement learning.

Although the present invention has been described in connection with certain preferred embodiments, it should be understood that it is not intended to limit disclosure to those particular embodiments. Instead, it is intended to cover all possible alternatives, modifications and equivalents within the spirit and scope of the invention, as defined by the appended claims.

What is claimed is:

1. A method for predicting maximal oxygen uptake in a wearable device, comprising:
   receiving information of user profile of a user;
   capturing temporal inputs including heart rate and speed readings;
   split the temporal inputs into n-second time windows; and
   processing the temporal inputs using a feature extraction module, which includes:
      identifying points where heart rate and speed signals are stable, where signal stability is calculated by using a threshold on a standard deviation of a signal sampled at 1 Hz;
      calculating the standard deviation of a temporal signal with a moving average $\bar{x}_{A \to A+M}$, Which is an average of the temporal signal with a sliding window of M seconds with a stride of N seconds;
      calculating the moving average by storing M and N variables;
      calculating the standard deviation of the temporal signal with a sliding window of M seconds with a stride of N seconds starting at a second A;
      calculating the moving standard deviation by storing 2*M and N variables;
   making a prediction by combining two or more multilayer perceptron artificial neural networks (MLP), with each MLP containing a hidden layer, where the prediction is based on a verification of a predicted value against a predefined threshold τ according to a range of tolerance values for each MLP;
   fusing a linear regression and an MLP prediction for each n-second stable region as follows:

$$VO_2Max'_\tau = \frac{(VO_2Max_{LR} + VO_2Max_{MLP})}{2}$$

where $VO_2Max_\tau'$ is the fused prediction for the window τ, $VO_2Max_{LR}$ is the prediction of linear regression and $VO_2Max_{MLP}$ is the prediction of MLP;
   calculating a percentage of theoretical maximum heart rate (pHR) as follows:

$$pHR = \frac{\overline{HR}}{211 - 0.64 * Age}$$

where $\overline{HR}$ is an average of heart rate readings in a n-second window and a denominator is an estimation of a maximum heart rate according to age;
   assigning one weight$_\tau$ according to the percentage of theoretical maximum heart rate (pHR);
   where new weight for a last prediction shown to the user is:

$$weight_{\tau-1} = \max\left(0, weight'_{\tau-1} * \left[1 - \frac{\text{days since the last prediction}}{30}\right]\right)$$

predicting VO$_2$Max using machine learning sets based on pattern detection whereby a weighted sum VO$_2$Max$_\tau$' with previous VO$_2$Max predictions is performed to merge predictions of the machine learning sets and obtain VO$_2$Max output per time as follows:

$$VO_2Max_\tau = \frac{weight_\tau * VO_2Max'_\tau + weight_{\tau-1} * VO_2Max_{\tau-1}}{(weight_\tau + weight_{\tau-1})}$$

where weight$_\tau$ is a computed weight for a current stable region, weight$_{\tau-1}$ is a cumulative weight until the previous stable region, VO$_2$Max'τ is a current prediction, and VO$_2$Max$_{\tau-1}$ is a last computed prediction.

2. The method according to claim 1, the information of the user profile includes age, gender, height and weight of the user.

3. The method according to claim 1, wherein, two temporal inputs composed of the heart rate and speed readings are split into n-second time windows without overlap.

4. The method according to claim 1, further comprising:
   waiting for temporal data of a next n-second window when the heart rate and speed signals are unstable based on a standard deviation being above a predefined threshold.

5. The method according to claim 1, comprising:
   performing the prediction of maximal oxygen uptake as VO$_2$Max as follows:

$$VO2Max = n_0 + (n_1*G) + (n_2*S) - (n_3*W) - (n_4*HR) - (n_5*A) + (n_6*HR/S)$$

where VO$_2$Max is in ml/min/Kg, G refers to gender whereby female=0 and male=1, S refers to speed in Km/h, W refers to weight in Kg, HR refers to heart rate in beats per minute, A refers to age in years and $n_0$ to $n_6$ referring to constant values used for adjustment based on coefficients of the linear regression.

6. The method according to claim 1, wherein a first MLP includes a hidden layer with two neurons that has been trained with individuals who have VO$_2$Max less than τ+tolerance.

7. The method according to claim 1, wherein provided a result of a first MLP is greater than T, the prediction is given by a second MLP.

8. The method according to claim 1, wherein a second MLP includes a hidden layer with two neurons that trained with subjects that have VO$_2$Max greater than T+tolerance.

9. The method according to claim 1, further comprising:
   updating the weight$_\tau$' value by considering a minimum between the sum of an accumulated weight plus the weight adopted for the last computation and the MaxWeight:

$$weight'_\tau = \min(weight'_{\tau-1} + weight_\tau, MaxWeight)$$

where weight'$_{\tau-1}$ is the accumulated weight up to the previous stable region and weight$_\tau$ is the weight adopted for the last VO$_2$Max computation.

10. The method according to claim 1, wherein value displayed to the user is updated according to the last value displayed to user U (x) and the last prediction of the P (k+n) algorithm, where:

$$dU = f(U(x), P(k+n))$$

$$U(x+1) = dU + U(x)$$

where x refers to each session, U refers to the user, x+1 refers to the value presented to the user that is updated, n refers to a stable region, k refers to a new stable region and a function $f$ is defined as a function as follows:

$$|f(U(x), P(k+n))| \le |P(k+n) - U(x)|; \text{ and}$$

$$\frac{P(k+n) - U(x)}{|P(k+n) - U(x)|} = \frac{f(U(x)P(k+n))}{|f(U(x)P(k+n))|}.$$

* * * * *